United States Patent
Gono

(10) Patent No.: US 8,842,285 B2
(45) Date of Patent: Sep. 23, 2014

(54) OPTICAL MEASUREMENT APPARATUS AND OPTICAL MEASUREMENT SYSTEM

(71) Applicant: Olympus Medical Systems Corp., Tokyo (JP)

(72) Inventor: Kazuhiro Gono, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/085,132

(22) Filed: Nov. 20, 2013

(65) Prior Publication Data

US 2014/0146320 A1    May 29, 2014

Related U.S. Application Data

(63) Continuation of application No. PCT/JP2013/068649, filed on Jul. 8, 2013.

(60) Provisional application No. 61/681,386, filed on Aug. 9, 2012.

(51) Int. Cl.
*G01N 21/55*     (2014.01)
*G01N 21/47*     (2006.01)
*G01N 21/84*     (2006.01)
*A61B 5/00*      (2006.01)

(52) U.S. Cl.
CPC ............... *G01N 21/47* (2013.01); *G01N 21/84* (2013.01); *A61B 5/0084* (2013.01)
USPC ........................................................ 356/445

(58) Field of Classification Search
CPC .................................................... G01N 21/55
USPC ........................................................ 356/445
See application file for complete search history.

(56) References Cited

U.S. PATENT DOCUMENTS 4,600,923 A * 7/1986 Hicks et al. .............. 340/870.02
4,722,340 A * 2/1988 Takayama et al. ................ 601/4
(Continued)

FOREIGN PATENT DOCUMENTS

JP   A-2002-291764   10/2002
JP   A-2005-134537   5/2005
(Continued)

OTHER PUBLICATIONS

Aug. 20, 2013 International Search Report issued in International Application No. PCT/JP2013/068649 (with translation).

*Primary Examiner* — Roy M Punnoose
(74) *Attorney, Agent, or Firm* — Oliff PLC

(57) ABSTRACT

An optical measurement apparatus is configured to detachably connect to a measurement probe for performing optical measurement by receiving and outputting light from a tip of the measurement probe. The optical measurement apparatus includes a computation unit configured to compute intensity of the light inputted to the measurement probe, and output the intensity as measurement data, a recording unit configured to record the measurement data of at least one subject, a reset controller configured to perform control of deleting the measurement data recorded in the recording unit and resetting the recording unit, and a detector which is provided at a connection part between the optical measurement apparatus and the measurement probe, and which is configured to detect that the measurement probe is attached to the optical measurement apparatus and cause the reset controller to be in an on state according to the detection.

3 Claims, 2 Drawing Sheets

(56) References Cited

U.S. PATENT DOCUMENTS

| | | | |
|---|---|---|---|
| 8,158,883 B2* | 4/2012 | Soffer | 174/50 |
| 2006/0234524 A1* | 10/2006 | Abadia | 439/74 |
| 2006/0265732 A1* | 11/2006 | Nakanishi et al. | 725/136 |
| 2007/0250006 A1 | 10/2007 | Court et al. | |
| 2011/0151410 A1* | 6/2011 | Jung et al. | 433/215 |

FOREIGN PATENT DOCUMENTS

| | | |
|---|---|---|
| JP | A-2006-006515 | 1/2006 |
| JP | A-2006-158716 | 6/2006 |
| JP | A-2008-029521 | 2/2008 |
| JP | A-2009-530063 | 8/2009 |
| JP | A-2010-286765 | 12/2010 |

* cited by examiner

OPTICAL MEASUREMENT APPARATUS AND OPTICAL MEASUREMENT SYSTEM

CROSS-REFERENCE TO RELATED APPLICATIONS

This application is a continuation of International Application No. PCT/JP2013/068649, designating the United States and filed on Jul. 8, 2013 which claims the benefit of priority from U.S. provisional application No. 61/681,386 filed on Aug. 9, 2012, and the entire contents of the International application and the United States provisional application are incorporated herein by reference.

BACKGROUND OF THE INVENTION

1. Field of the Invention

The present invention relate to an optical measurement apparatus and an optical measurement system which measure optical characteristics of body tissues.

2. Description of the Related Art

Conventionally, an optical measurement system is known which radiates illumination light on a sample such as body tissues of a subject, and estimates the property of the sample based on a measurement value of detection light reflected or scattered from the sample, as disclosed in Japanese Laid-open Patent Publication No. 2002-291764 and Japanese Laid-open Patent Publication No. 2006-158716, for example. Such an optical measurement system includes an optical measurement apparatus which has a light source which emits illumination light to a sample, a detector which detects detection light (return light) from the sample and computes intensity of the light and a memory unit which associates and stores the light intensity and information about a measured subject, and a measurement probe which is attachable to and detachable from the optical measurement apparatus and is configured to irradiate the sample with illumination light and receive light from the sample. The measurement probe is replaced depending on subject to perform measurement.

SUMMARY OF THE INVENTION

An optical measurement apparatus according to one aspect of the invention is configured to detachably connect to a measurement probe for performing optical measurement by receiving and outputting light from a tip of the measurement probe. The optical measurement apparatus includes: a computation unit configured to compute intensity of the light inputted to the measurement probe, and output the intensity as measurement data; a recording unit configured to record the measurement data of at least one subject; a reset controller configured to perform control of deleting the measurement data recorded in the recording unit and resetting the recording unit; and a detector which is provided at a connection part between the optical measurement apparatus and the measurement probe, and which is configured to detect that the measurement probe is attached to the optical measurement apparatus and cause the reset controller to be in an on state according to the detection.

An optical measurement system according to another aspect of the invention includes a measurement probe configured to perform optical measurement by receiving and outputting light from a tip of the measurement probe, and an optical measurement apparatus configured to detachably connect to the measurement probe. The optical measurement apparatus includes: a computation unit configured to compute intensity of the light inputted to the measurement probe, and output the intensity as measurement data; a recording unit configured to record the measurement data of at least one subject; a reset controller configured to perform control of deleting the measurement data recorded in the recording unit and resetting the recording unit; and a detector which is provided at a connection part between the optical measurement apparatus and the measurement probe, and which is configured to detect that the measurement probe is attached to the optical measurement apparatus and cause the reset controller to be in an on state according to the detection.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
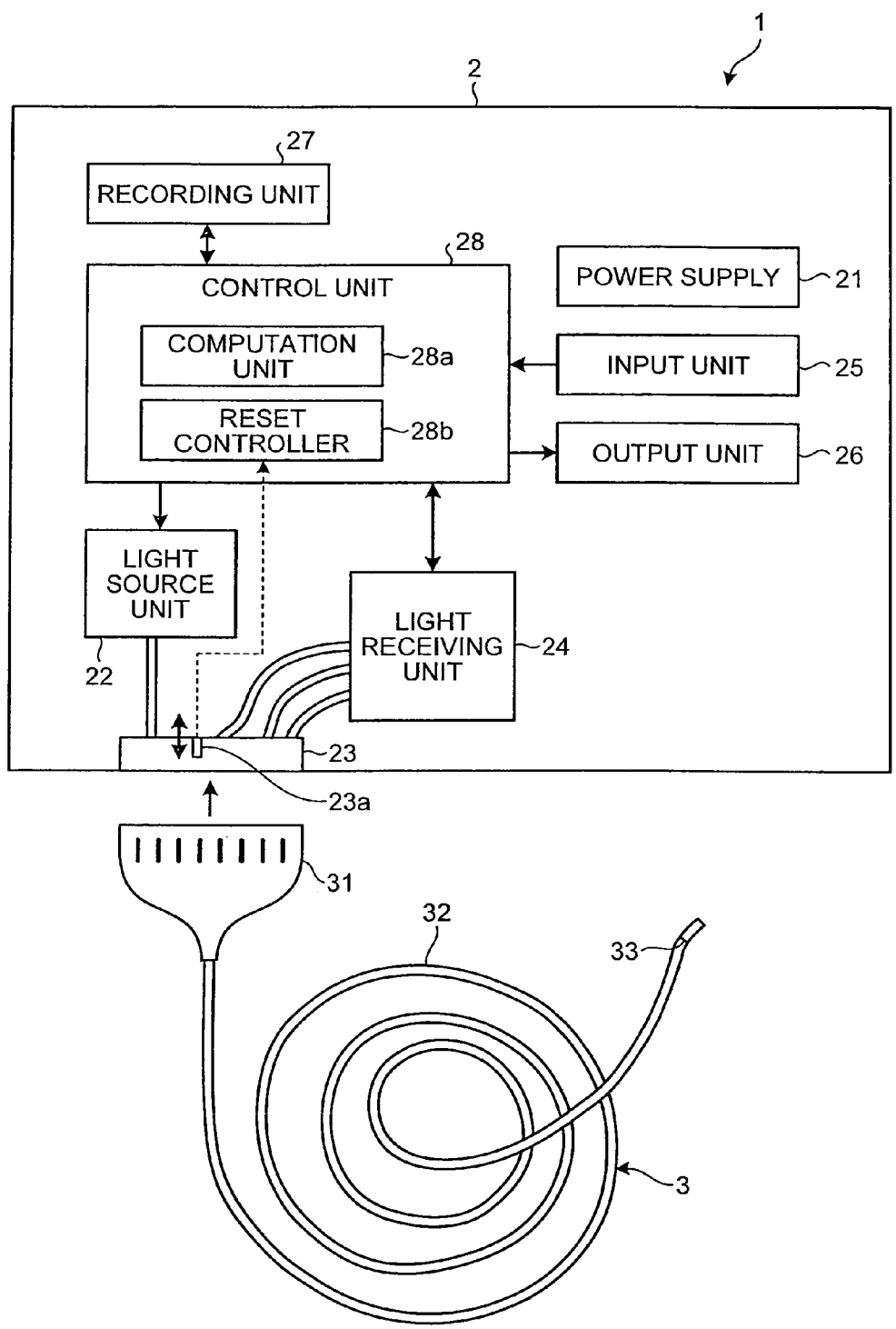
FIG. 1 is a block diagram schematically illustrating a configuration of a living body optical measurement system according to an embodiment of the present invention.

Hereinafter, preferred embodiments of an optical measurement apparatus and an optical measurement system according to the present invention will be described in detail with reference to the drawings. The present invention is not limited by the embodiments. Further, the same portions will be described by assigning the same reference numerals in the drawings. Furthermore, it needs to be kept in mind that the drawings are schematic, and the relationship between the thickness and the width of each member and the ratio of each member are different from actual members. Still further, there are portions including a different relationship between dimensions and a different ratio even between the drawings.

FIG. 1 is a block diagram schematically illustrating a configuration of a living body optical measurement system according to an embodiment of the present invention. A living body optical measurement system 1 illustrated in FIG. 1 has a living body optical measurement apparatus 2 which optically measures a measurement target such as body tissues, which are scatters, and detects the property of the measurement target (characteristics), and a measurement probe 3 which is used for measurement and which is detachably connected to the living body optical measurement apparatus 2 and is inserted in a subject.

First, the living body optical measurement apparatus 2 will be described. The living body optical measurement apparatus 2 has a power supply 21, a light source unit 22, a connection part 23, a light receiving unit 24, an input unit 25, an output unit 26, a recording unit 27 and a control unit 28. The power supply 21 supplies power to each component of the living body optical measurement apparatus 2.

The light source unit 22 is realized by using, for example, an incoherence light source such as a white LED (Light Emitting Diode), a xenon lamp, a tungsten lamp or a halogen lamp, and one or a plurality of lenses where necessary such as condenser lenses or collimator lenses. The light source unit 22 outputs incoherent light which includes at least one spectrum component and which is radiated on a measurement target through the connection part 23, to the measurement probe 3.

The connection part 23 detachably connects a connector portion 31 of the measurement probe 3 to the living body optical measurement apparatus 2. The connection part 23 outputs light emitted from the light source unit 22, to the measurement probe 3, and outputs return light of illumination light, which is emitted from the measurement probe 3 and which is reflected and/or scattered by a measurement target, to the light receiving unit 24.

Further, the connection part 23 has a switch 23a which projects from a surface of the connection part 23 in which the measurement probe 3 is attached, and is provided movably with respect to this attaching surface. The switch 23a is pushed when the measurement probe 3 is attached to the connection part 23, and is pushed in the connection part 23. When pushed in, the switch 23a detects that the measurement probe 3 is attached to the connection part 23, and causes a reset controller 28b to be in an on state which will be described below.

The light receiving unit 24 receives and measures return light of illumination light which is emitted from the measurement probe 3 and which is reflected and/or scattered by a measurement target. The light receiving unit 24 is realized by using, for example, a plurality of spectrometers and light receiving sensors. More specifically, in the light receiving unit 24, the number of spectrometers corresponds to the number of light receiving fibers of the measurement probe 3 which will be described below. The light receiving unit 24 measures a spectrum component and an intensity distribution of scattering light incident from the measurement probe 3, and measures each wavelength. The light receiving unit 24 outputs a measurement result to the control unit 28.

The input unit 25 receives an input of an instruction signal for instructing activation of the living body optical measurement apparatus 2 or an instruction signal for instructing other various operations and outputs the instruction signal to the control unit 28. The input unit 25 is realized by using, for example, a push-type switch or a touch panel.

The output unit 26 outputs information related to various processing in the living body optical measurement apparatus 2. Further, the output unit 26 displays a numerical value such as intensity of light received by the light receiving unit 24 (a characteristic value computed by a computation unit 28a described below), on a display under control of the control unit 28. The output unit 26 is realized by using, for example, a liquid crystal or organic EL (Electro Luminescence) display and speakers. A configuration may be employed where these numerical values are printed and this printed material is outputted.

The recording unit 27 is realized by using volatile memory or non-volatile memory, and records various programs for operating the living body optical measurement apparatus 2, and various items of data and various parameters used for optical measurement processing. The recording unit 27 temporarily records information which is obtained during processing in the living body optical measurement apparatus 2. Further, the recording unit 27 associates and records a measurement result obtained by the living body optical measurement apparatus 2 and subject information of a subject which is a measurement target (for example, a specimen ID, examination item information and an examination date). The recording unit 27 may be configured by using, for example, a memory card attached from an outside of the living body optical measurement apparatus 2.

The control unit 28 is configured by using, for example, a CPU (Central Processing Unit). The control unit 28 controls a processing operation of each unit of the living body optical measurement apparatus 2. The control unit 28 controls the operation of the living body optical measurement apparatus 2 by, for example, transferring instruction information corresponding to each unit of the living body optical measurement apparatus 2 or data. The control unit 28 controls the operation of the light source unit 22, and records the measurement result of the light receiving unit 24 in the recording unit 27. The control unit 28 has the computation unit 28a and the reset controller 28b.

The computation unit 28a performs a plurality of computation processing based on the measurement result of the light receiving unit 24, and computes a characteristic value related to the property of a measurement target. The type of this characteristic value is set according to, for example, an instruction signal received by the input unit 25.

The reset controller 28b performs control of deleting and resetting a measurement result in the recording unit 27 in response to an input of a signal from the switch 23a. Further, the reset controller 28b resets the recording unit 27 when the above-described switch 23a is pushed and the switch 23a causes the reset controller 28b to be in the on state.

Next, the measurement probe 3 will be described. The measurement probe 3 is realized by disposing a plurality of optical fibers inside. More specifically, the measurement probe 3 is realized by using an illumination fiber which emits illumination light to a measurement target, and a plurality of light receiving fibers on which return light of illumination light reflected and/or scattered by the measurement target is incident at different angles. The measurement probe 3 has a connector portion 31 which is detachably connected to the connection part 23 of the living body optical measurement apparatus 2, a flexible portion 32 which has flexibility, and a tip portion 33 which is provided with an optical element at a tip, and which radiates illumination light supplied from the light source unit 22 and receives return light from a measurement target.

The measurement probe 3 has an illumination fiber which radiates illumination light on a measurement target, and light receiving fibers on which return light of the illumination light reflected and/or scattered by the measurement target is incident. Further, the illumination fiber and the light receiving fibers are covered by a glass or resin to prevent damages thereon and fix positions thereof. Furthermore, a covering member adopts a structure in which an outer periphery is covered with a glass or brass to protect the fibers from an external force, and the outer periphery is further covered by a probe outer casing such as SUS.

The illumination fiber is formed by using, for example, a step-index single core fiber. The illumination fiber transmits illumination light outputted from the light source unit 22, and radiates the illumination light on a measurement target through the optical element. The number of illumination fibers can be adequately changed according to an examination item or a type of a measurement target such as a blood current or a site.

The light receiving fibers are each formed by using, for example, a step-index single core fiber. The light receiving fibers each transmits return light of illumination light which is incident on each tip through the optical element and which is reflected and/or scattered by a measurement target, and outputs the light to the light receiving unit 24 of the living body optical measurement apparatus 2. The number of light receiving fibers can be adequately changed according to an examination item or a type of a measurement target such as a blood current or a site.

The optical element has a columnar shape, and is formed by using a transmissive glass having a predetermined refractive index. The optical element is formed to fix the distance between the illumination fiber and a measurement target, and radiate light in a state where a spatial coherent length is fixed. Further, the optical element is formed to fix the distances between the light receiving fibers and the measurement target, and stably receive return light at a predetermined scattering angle.

Figure 2:
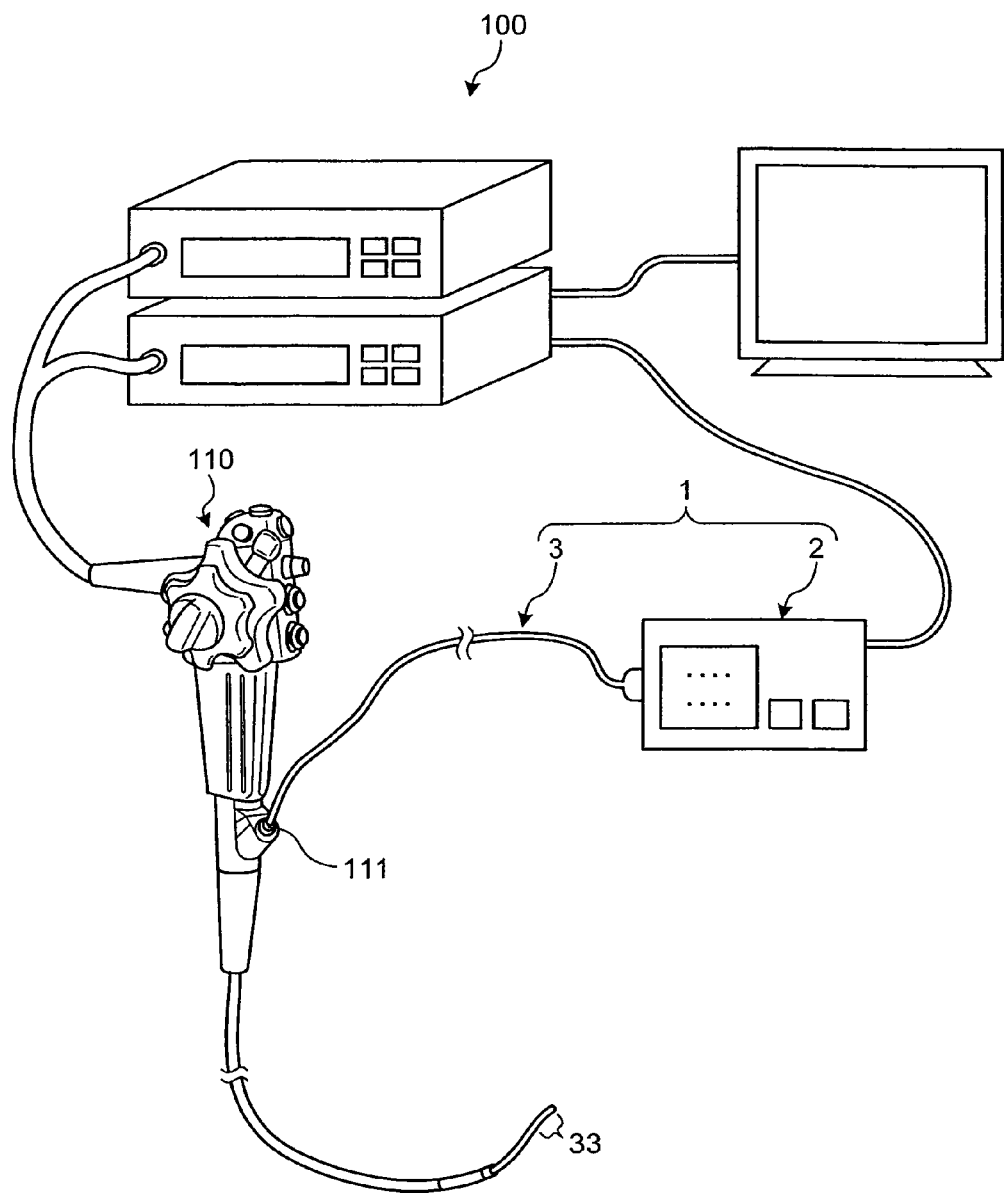
FIG. 2 is a view illustrating a situation in which the living body optical measurement system according to an embodiment of the present invention is used in an endoscope system.

As illustrated in FIG. 2, with the living body optical measurement system 1 configured as described above, the measurement probe 3 is inserted in a subject through a treatment tool channel 111 provided in an endoscope apparatus 110 (endoscope) of an endoscope system 100, the illumination fiber radiates illumination light on a measurement target, and the light receiving fibers each receive return light of illumination light reflected and/or scattered by the measurement target, at different scattering angles and transmit the light to the light receiving unit 24 of the living body optical measurement apparatus 2. Then, the computation unit 28a computes a characteristic value of the property of the measurement target based on the measurement result of the light receiving unit 24.

Meanwhile, when the measurement probe 3 is replaced, that is, when the new measurement probe 3 is attached to the living body optical measurement apparatus 2, the switch 23a is pushed. When the switch 23a is pushed, the reset controller 28b is brought into an on state by the switch 23a, and deletes a measurement result such as light intensity data recorded in the recording unit 27.

By this means, when the new measurement probe 3 is attached to perform measurement, a measurement result of a different subject which was previously measured is deleted, so that a measurement result which is currently measured is not associated with a different subject and recorded.

When the reset controller 28b deletes data in the recording unit 27, setting data related to a processing operation of each unit of the living body optical measurement apparatus 2 is preferably left recorded in the recording unit 27 without being deleted. Further, when there is setting data related to the measurement probe 3, this setting data may be left without being deleted, or the setting data may be deleted and new setting data may be acquired from the attached measurement probe 3.

According to the above-described embodiments of the present invention, the switch 23a is provided in the connection part 23 which connects with the measurement probe 3, when the measurement probe 3 is attached to the connection part 23 and the switch 23a is pushed, the switch 23a causes the reset controller 28b to be in the on state, and the reset controller 28b which has been brought into the on state deletes and resets a measurement result such as light intensity data recorded in the recording unit 27, so that it is possible to reliably associate subject information with measurement data.

Further, according to the embodiments, the measurement probe 3 is attachable to and detachable from the living body optical measurement apparatus 2, so that the measurement probe 3 is disposable, the measurement probe 3 does not need to be sterilized at medical facilities, and the measurement probe 3 may have comparatively poor durability and, consequently, it is possible to reduce cost of the measurement probe 3.

Although, when the switch 23a is pushed, a signal indicating that the measurement probe 3 is attached is outputted with the above-described embodiments, for example, information unique to this measurement probe 3 (for example, an identification number) may be acquired when the measurement probe 3 is attached without providing the switch 23a, and a measurement result in the recording unit may be deleted when this information is inputted in the reset controller 28b.

As described above, an optical measurement apparatus and an optical measurement system according to the present invention are useful in reliably associating subject information with measurement data.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical measurement apparatus configured to detachably connect to a measurement probe for performing optical measurement by receiving and outputting light from a tip of the measurement probe, the optical measurement apparatus comprising:
   a computation unit configured to compute intensity of the light inputted to the measurement probe, and output the intensity as measurement data;
   a recording unit configured to record the measurement data of at least one subject;
   a reset controller configured to perform control of deleting the measurement data recorded in the recording unit and resetting the recording unit; and
   a detector which is provided at a connection part between the optical measurement apparatus and the measurement probe, and which is configured to detect that the measurement probe is attached to the optical measurement apparatus and cause the reset controller to be in an on state according to the detection.

2. The optical measurement apparatus according to claim 1, wherein the detector is a switch which is provided movably with respect to a surface of the connection part to which the measurement probe is attached, and, when the measurement probe is attached, the switch is pushed in the connection part and causes the reset controller to be in the on state.

3. An optical measurement system comprising:
   a measurement probe configured to perform optical measurement by receiving and outputting light from a tip of the measurement probe; and
   an optical measurement apparatus configured to detachably connect to the measurement probe, wherein
   the optical measurement apparatus comprises:
   a computation unit configured to compute intensity of the light inputted to the measurement probe, and output the intensity as measurement data;
   a recording unit configured to record the measurement data of at least one subject;
   a reset controller configured to perform control of deleting the measurement data recorded in the recording unit and resetting the recording unit; and
   a detector which is provided at a connection part between the optical measurement apparatus and the measurement probe, and which is configured to detect that the measurement probe is attached to the optical measurement apparatus and cause the reset controller to be in an on state according to the detection.

* * * * *